United States Patent [19]

Raphael

[11] 4,102,896
[45] Jul. 25, 1978

[54] PREPARATION OF A 5-(2,2-DIHALOVINYL)-4,4-DIMETHYL-2-OXOTETRAHYDROFURAN

[75] Inventor: Ralph Alexander Raphael, Cambridge, England

[73] Assignee: Imperial Chemical Industries Limited, London, England

[21] Appl. No.: 689,934

[22] Filed: May 25, 1976

[30] Foreign Application Priority Data

May 27, 1975 [GB] United Kingdom ............ 23153/75

[51] Int. Cl.² .................................................. C07D 307/32
[52] U.S. Cl. ........................... 260/343.6; 260/514 H; 260/585.5; 260/586 R; 560/123
[58] Field of Search ........................................ 260/343.6

[56] References Cited

U.S. PATENT DOCUMENTS

| | | | |
|---|---|---|---|
| 3,488,732 | 1/1970 | Heiba et al. | 260/343.6 |
| 3,946,078 | 3/1976 | Rautenetrauch et al. | 260/586 R |
| 3,962,148 | 6/1976 | Hochstetler et al. | 252/522 |

Primary Examiner—Cecilia M. Jaisle
Attorney, Agent, or Firm—Cushman, Darby & Cushman

[57] ABSTRACT

A process for preparing a 5-(2,2-dihalovinyl)-4,4-dimethyl-2-oxotetrahydrofuran of formula:

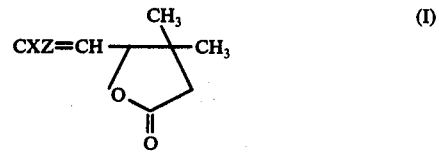

(I)

wherein X and Z are each either chlorine or bromine, which comprises the step of treating a compound of formula:

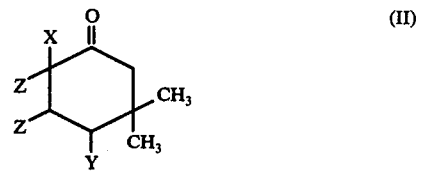

(II)

with an excess of a base selected from alkali metal hydroxides and chemical equivalents thereof.

8 Claims, No Drawings

PREPARATION OF A 5-(2,2-DIHALOVINYL)-4,4-DIMETHYL-2-OXOTETRAHYDROFURAN

This invention relates to a process for the preparation of certain lactones useful as intermediates in the manufacture of insecticides. More particularly it relates to a process for the preparation of 5-(2,2-dihalovinyl)-4,4-dimethyl-2-oxotetrahydrofurans, which may be converted to 2-(2,2-dihalovinyl)-3,3-dimethyl cyclopropane carboxylates.

2-(2,2-Dichlorovinyl)-3,3-dimethylcyclopropane carboxylic acid is an important intermediate in the production of insecticides, including, for example, 3-phenoxybenzyl 2-(2,2-dichlorovinyl)-3,3-dimethylcyclopropane carboxylate. The preparation of 2-(2,2-dichlorovinyl)-3,3-dimethylcyclopropane carboxylic acid has been described by Farkas et al (Collection Czechoslov. Chem. Commun., (1959), 24, pp 2230–2236) by the reaction of ethyl diazoacetate with 1,1-dichloro-4-methyl-1,3-pentadiene followed by hydrolysis of the resultant ethyl ester. This process is not suitable for large scale preparation of the acid because of the difficulties of working with ethyl diazoacetate, which is a substance which can explosively decompose unless the conditions are rigorously controlled, and which is believed to be a potent carcinogen.

We have devised a process for the preparation of esters of 2-(2,2-dihalovinyl)-3,3-dimethylcyclopropane carboxylic acid from the corresponding 5-(2,2-dihalovinyl)-4,4-dimethyl-2-oxotetrahydrofuran. This invention relates to a method for the preparation of these valuable intermediates.

Accordingly the present invention provides a process for preparing a 5-(2,2-dihalovinyl)-4,4-dimethyl-2-oxotetrahydrofuran of formula:

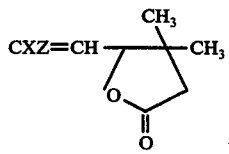

(I)

wherein X and Z are each either chlorine or bromine, which comprises the step of treating a compound of formula:

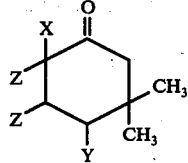

(II)

with an excess of a base selected from alkali metal hydroxides and chemical equivalents thereof.

Sodium and potassium hydroxides are preferred.

One chemical equivalent is treatment of the compound of formula II with an alkali metal hydride and thereafter bringing the product of alkali metal hydride treatment into contact with water. Sodium hydride is a preferred alkali metal hydride.

A preferred method of treatment with alkali metal hydroxides is to carry out the reaction in a heterogeneous system in which the compound of formula II is in solution in a water immiscible solvent, for example chloroform or dichloromethane, and the hydroxide is in aqueous solution, the reaction being conducted in the presence of a phase transfer catalyst such as a quaternary ammonium salt, for example benzyltrimethylammonium bromide or tetrabutylammonium chloride.

All the above reactions may be carried out at a temperature within the range of 0° to 100° C, preferably within the range 0° to 35° C.

Examples of compounds of formula I which may be obtained by the invention process are:

5-(2,2-dichlorovinyl)-4,4-dimethyl-2-oxotetrahydrofuran, 5-(2,2-dibromovinyl)-4,4-dimethyl-2-oxotetrahydrofuran, and 5-(2-bromo-2-chlorovinyl)-4,4-dimethyl-2-oxotetrahydrofuran.

As noted above these compounds may be converted to the corresponding 2-(2,2-dihalovinyl)-3,3-dimethylcyclopropane carboxylic acid esters, and although the dichlorovinyl and dibromovinyl cyclopropane derivatives may also be obtained by other processes, the invention process allows for the first time a preparative method for obtaining the mixed bromochlorovinyl analogues.

The mechanism by which the invention process proceeds is not fully understood, but may involve the formation of a ketene intermediate of formula:

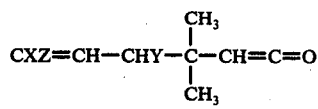

although it is possible to postulate mechanisms which do not involve this intermediate.

The compounds of formula II used in the above step of the invention process may be prepared from 5,5-dimethylcyclohex-2-enone by a series of steps involving halogenation and dehydrohalogenation.

Thus 5,5-dimethylcyclohex-2-enone (III) may be halogenated with chlorine or bromine to yield a compound of formula IV which on treatment with base yields a compound of formula V as follows:

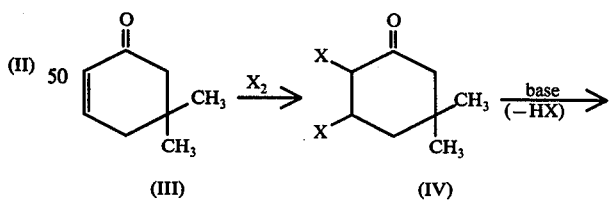

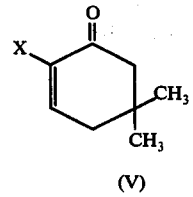

(V)

The compound of formula V on treatment with a source of positive halogen, for example an N-haloimide, gives a compound of formula VI which may be treated with halogen to yield the compound of formula II, as follows:

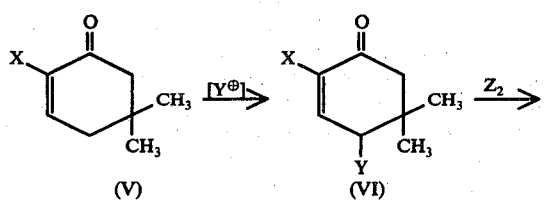

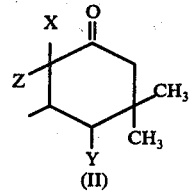

In a further aspect the invention provides a process of preparing a compound of formula I which comprises the steps of (a) treating 5,5-dimethylcyclohex-2-enone with a halogen of formula $X_2$ to obtain a compound of formula:

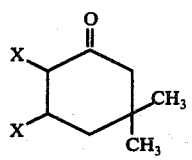
(IV)

(b) either treating the compound of formula IV with one molar equivalent of a base or heating a compound of formula IV under reduced pressure to obtain a compound of formula:

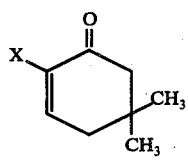
(V)

(c) subjecting the compound of formula V to treatment with a source of positive halogen to obtain a compound of formula:

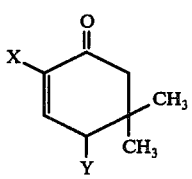
(VI)

(d) treating the compound of formula VI with halogen of formula $Z_2$ to obtain a compound of formula:

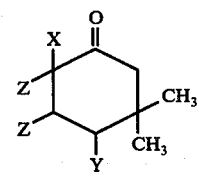
(II)

and (e) treating the compound of formula II with at least two moles of a base to obtain the compound of formula I; wherein, X, Y and Z are independently selected from chlorine atoms and bromine atoms, and $X_2$ and $Z_2$ are independently selected from molecular chlorine and molecular bromine.

A suitable source of positive halogen for use in step (c) of the above process is an N-haloamide or N-haloimide. Preferred compounds of this type are N-chlorosuccinimide and N-bromosuccinimide.

The compounds of formula II, IV, V and VI are all novel.

In a yet further aspect therefore the invention provides (i) compounds of formula:

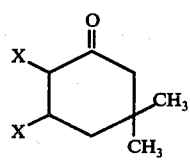
(IV)

wherein X is chlorine or bromine, and a process for preparing them as set out in step (a) of the invention process set out immediately hereinabove;

(ii) compounds of formula:

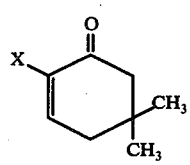
(V)

wherein X is chlorine or bromine, and a process for preparing them as set out in step (b) of the invention process set out immediately hereinabove;

(iii) compounds of formula:

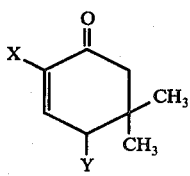
(VI)

wherein X and Y are independently chlorine or bromine, and a process for preparing them as set out in step (c) of the invention process set out immediately hereinabove; and (iv) compounds of formula:

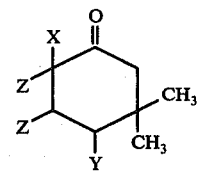
(II)

wherein X, Y and Z are independently chlorine or bromine, and a process for preparing them as set out in step (d) of the invention process set out immediately hereinabove.

Examples of the novel compounds of formula IV are 2,3-dichloro-5,5-dimethylcyclohexanone and 2,3-dibromo-5,5-dimethylcyclohexanone.

Examples of the novel compounds of formula V are 2-chloro-5,5-dimethylcyclohex-2-enone and 2-bromo-5,5-dimethylcyclohex-2-enone.

Examples of the novel compounds of formula VI are 2,4-dichloro-5,5-dimethylcyclohex-2-enone,
4-bromo-2-chloro-5,5-dimethylcyclohex-2-enone,
2-bromo-4-chloro-5,5-dimethylcyclohex-2-enone, and
2,4-dibromo-5,5-dimethylcyclohex-2-enone.

Examples of the novel compounds of formula II are 2,2,3,4-tetrachloro-5,5-dimethylcyclohexanone,
2,3-dibromo-2,4-dichloro-5,5-dimethylcyclohexanone,
4-bromo-2,2,3-trichloro-5,5-dimethylcyclohexanone,
2-chloro-2,3,4-tribromo-5,5-dimethylcyclohexanone,
2-bromo-2,3,4-trichloro-5,5-dimethylcyclohexanone,
4-chloro-2,2,3-tribromo-5,5-dimethylcyclohexanone,
2,4-dibromo-2,3-dichloro-5,5-dimethylcyclohexanone, and
2,2,3,4-tetrabromo-5,5-dimethylcyclohexanone.

As stated above the compounds of formula I obtained by the invention process are valuable intermediates which may be converted to compounds of formula:

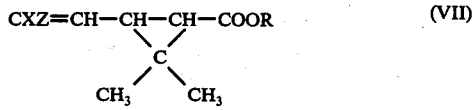

where R is a lower alkyl group. This conversion, which is set out in more detail in our copending UK patent application No. 29253/75, may be achieved by the steps of treating the compound of formula I with an inorganic acid halide, such as for example thionyl chloride, and treating the product obtained with a lower alcohol of formula ROH to obtain a compound of formula:

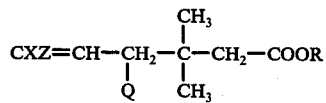

where Q is halogen. This compound on treatment with base gives the compound of formula VII where R is lower alkyl. Compounds of formula VII obtained in this way from compounds of formula I are the lower alkyl esters of 2-(2,2-dichlorovinyl)-3,3-dimethylcyclopropane carboxylic acid, 2-(2-chloro-2-bromovinyl)-3,3-dimethylcyclopropane carboxylic acid, and 2-(2,2-dibromovinyl)-3,3-dimethylcyclopropane carboxylic acid.

These lower alkyl esters may be converted by conventional techniques, for example via the acid, and acid chloride, to compounds of formula VII where R is, for example, 3-phenoxybenzyl, or 5-benzyl-3-furylmethyl, which are useful as insecticides.

The invention is illustrated by the following Examples.

EXAMPLE 1

This example illustrates the preparation of 5,5-dimethylcyclohex-2-enone (III) from dimedone.

(a) Preparation of 3-chloro-5,5-dimethylcyclohex-2-enone.

A mixture of dimedone (50.0 g), phosphorus pentachloride (34.25 g) and dry chloroform (400 ml) was heated at the reflux temperature for a period of 2.5 hours, after which it was kept at the ambient temperature for 18 hours. After removal of the chloroform by evaporation under reduced pressure, the residue was mixed with water and ice and extracted with diethyl ether (3 × 100 ml). The combined ethereal extracts were washed with dilute potassium hydroxide and with water. The combined washings were extracted with fresh ether and these extracts combined with the washed ethereal extracts, and the whole dried over anhydrous magnesium sulphate. The ethereal extract was concentrated by evaporation under reduced pressure, and the residual oil purified by distillation to yield 3-chloro-5,5-dimethylcyclohex-2-enone, b.p. 94° C/15 mm Hg. The infra-red spectrum (liquid film) showed main absorption bands at 3000, 1700, 1620, 1360, 1310, 1160, 1010, 910 and 850 $cm^{-1}$.

N.m.r. ($CDCl_3$): 8.92$\tau$(s), 6H; 7.8$\tau$(s), 2H; 7.5$\tau$(d), 2H; and 3.85$\tau$(t), 1H.

(b) Preparation of 5,5-dimethylcyclohex-2-enone (III).

Activated zinc dust (15.0 g) was added to a stirred solution of 3-chloro-5,5-dimethylcyclohex-2-enone (9.0 g) and potassium iodide (7.5 g) in methanol (50 ml). After stirring for a period of 18 hours the mixture was filtered and the filtrate concentrated by evaporation under reduced pressure. The residue was mixed with dilute (8% w/v) hydrochloric acid and extracted with diethyl ether (2 × 100 ml). The combined ethereal extracts were washed with water and dried over anhydrous magnesium sulphate. After removal of the ether by evaporation under reduced pressure the residual oil was purified by distillation. 5,5-Dimethylcyclohex-2-enone was obtained as a pale yellow oil, b.p. 75° C/17 mm Hg.

Infra-red (liquid film): 3000, 1700, 1640, 1400, 1260, 1180 and 910 $cm^{-1}$.

N.m.r. ($CDCl_3$): 9.0$\tau$(s), 6H; 7.8$\tau$(s), 4H;, 4.0–4.2$\tau$(2t), 1H; 3.0–3.35$\tau$(m), 1H.

EXAMPLE 2

This example illustrates the preparation of 2-chloro-5,5-dimethylcyclohex-2-enone.

5,5-Dimethylcyclohex-2-enone (10.0 g) and glacial acetic acid (30 ml) were stirred together at 0° C and chlorine gas was bubbled into the mixture until one molar equivalent (5.73 g) had been absorbed. The temperature during the addition rose to 25° C. The mixture was partitioned between iced water and diethyl ether, and the ethereal layer separated, washed with wter and dried over anhydrous magnesium sulphate. Careful evaporation of the ether at low temperature under reduced pressure yield 2,3-dichloro-5,5-dimethylcyclohex-2-enone (infra-red absorption (liquid film) at 1750 $cm^{-1}$), but upon warming under reduced pressure evolution of hydrogen chloride was noted. When this evolution had stopped the residual oil was taken up in diethyl ether, washed with saturated sodium bisulphate sulution, and with water and dried over anhydrous magnesium sulphate. After evaporation of the ether under reduced pressure the residual oil was heated for several minutes at 100° C, and finally purified by distillation to yield 2-chloro-5,5-dimethylcyclohex-2-enone, b.p. 120°–124° C/16 mm Hg.

Infra-red (liquid film): 3000, 1700, 1630, 1490, 1350, 1030 and 960 $cm^1$.

N.m.r. (CDCl$_3$): 8.95τ(s), 6H; 7.7τ(d), 2H; 7.6τ(s), 2H; 3.0τ(t), 1H.

EXAMPLE 3

This example illustrates the preparation of 4-bromo-2-chloro-5,5-dimethylcyclohex-2-enone.

A mixture of 2-chloro-5,5-dimethylcyclohex-2-enone (1.58 g), N-bromosuccinimide (1.82 g), benzoyl peroxide (200 mg), and carbon tetrachloride (20 ml) was heated at the reflux temperature for a period of 18 hours whilst irradiating the mixture with a tungsten lamp. At the end of this period the precipitate was removed by filtration and the filtrate washed with dilute sodium bicarbonate solution and dried over anhydrous magnesium sulphate. The solvent was removed by evaporation under reduced pressure, the temperature being maintained below 40° C. The residual oil was identified by infra-red and n.m.r. as 4-bromo-2-chloro-5,5-dimethylcyclohex-2-enone.

Infra-red (liquid film): 3000, 1700, 1610, 1480, 1380, 1020, 950, 900 and 800 cm$^{-1}$.

N.m.r. (CDCl$_3$): 8.75τ(d), 6H; 7.4τ(q), 2H; 5.3τ(d), 1H; 2.85τ(d), 1H.

EXAMPLE 4

This example illustrates the preparation of 4-bromo-5,5-dimethyl-2,2,3-trichlorocyclohexanone.

Chlorine gas was passed into an ice-cooled stirred solution of 4-bromo-2-chloro-5,5-dimethylcyclohex-2-enone (2.0 g) in glacial acetic acid. After a few minutes a solid precipitate was formed, and the mixture temperature was allowed to rise to 20° C, at which point there was an exothermic reaction and the temperature rapidly rose to 30° C. Chlorine gas continued to be passed in to the mixture until a total of 0.8 g had been absorbed. The mixture was then poured into iced water and the precipitate which formed collected by filtration washed with water and the minimum quantity of ethanol and dried. Recrystallisation from ethanol yielded 4-bromo-5,5-dimethyl-2,2,3-trichlorocyclohexanone, m.p. 4-bromo-5,5-dimethyl-2,2,3-trichlorocyclohexanone, m.p. 117° C.

Infra-red ('Nujol'): 2950, 1750, 1470, 1380, 1210, 910 and 850 cm$^1$.

N.m.r. (CDCl$_3$): 8.8τ(d), 6H; 7.4τ(d), 1H; 6.7τ(d), 1H; 5.6τ(q), 2H. ('Nujol' is a Registered Trade Mark).

EXAMPLE 5

This example illustrates the preparation of 5-(2,2-dichlorovinyl)-4,4-dimethyl-2-oxotetrahydrofuran.

Sodium hydride (5 mg, obtained by washing 10 mg of a 50% dispersion in oil with petroleum ether) was suspended in dry toluene (2.0 ml) and 4-bromo-5,5-dimethyl-2,2,3-trichlorocyclohexanone (31 mg) added to the stirred suspension. After stirring for 30 minutes at the ambient temperature the mixture was refluxed for 18 hours. After cooling to the ambient temperature chloroform (10 ml) was added and the solution obtained washed with water and then dried over anhydrous magnesium sulphate. The solution was concentrated by evaporation of the solvents under reduced pressure. The residual oil was identified by comparison with an authentic sample by infra-red spectroscopy as being 5-(2,2-dichlorovinyl)-4,4-dimethyl-2-oxotetrahydrofuran.

Infra-red (liquid film): 3000, 1800, 1630, 1470, 1390, 1260, 1160, 1040, 1000 and 920 cm$^{-1}$.

EXAMPLE 6

This example also illustrates the preparation of 5-(2,2-dichlorovinyl)-4,4-dimethyl-2-oxotetrahydrofuran.

A mixture of 4-bromo-5,5-dimethyl-2,2,3-trichlorocyclohexanone (31 mg), benzyltrimethylammonium chloride (5 mg), dichloromethane (4 ml) and a solution of potassium hydroxide (27 mg) in water (4 ml) was stirred vigorously for 18 hours after which the aqueous phase was separated acidified with concentrated hydrochloric acid and extracted with chloroform. The chloroform extract was dried over anhydrous magnesium sulphate, and concentrated by evaporation of the solvent under reduced pressure. The residual oil was identified by infra-red spectroscopy as being identical with the product of Example 5.

EXAMPLE 7

This example illustrates the preparation of ethyl 2-(2,2-dichlorovinyl)-3,3-dimethylcyclopropane carboxylate from 5-(2,2-dichlorovinyl)-4,4-dimethyl-2-oxotetrahydrofuran.

A mixture of 5-(2,2-dichlorovinyl)-4,4-dimethyl-2-oxotetrahydrofuran (3.7 g) and thionyl chloride (8.4 g) was heated at the reflux temperature for 2.5 hours after which the excess thionyl chloride was distilled off at atmospheric pressure. When the mixture temperature reached 98° C the distillation was discontinued and the residue cooled to 40° to 50° C. Ethanol (7.0 ml) was added and the solution obtained added to a solution of sodium (0.85 g) in ethanol (25 ml) and the mixture stirred at the ambient temperature for 1 hour. The mixture was neutralised with aqueous hydrochloric acid, concentrated by evaporation under reduced pressure and the residue partitioned between water and toluene. After washing the toluene solution with water, it was dried over anhydrous magnesium sulphate and concentrated by evaporation under reduced pressure at 40° C. The liquid residue was shown by infra-red and nuclear magnetic resonance to comprise ethyl 2-(2,2-dichlorovinyl)-3,3-dimethylcyclopropane carboxylate in 82% yield. The product consisted of 25% of the cis-isomer and 75% of the trans-isomer.

I claim:

1. A process for the preparation of a compound of formula:

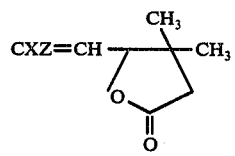

(I)

wherein X and Z are each either chlorine or bromine, which comprises the step of treating a compound of formula:

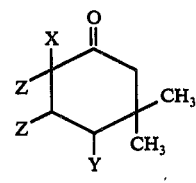

(II)

wherein Y is chlorine or bromine with either (A) an excess of an alkali metal hydroxide or (B) an excess of an alkali metal hydride followed by bringing the product of alkali metal hydride treatment in contact with water.

2. A process as claimed in claim 1 wherein the alkali metal hydroxide is sodium hydroxide or potassium hydroxide.

3. A process as claimed in claim 1 wherein the alkali metal hydride is sodium hydride.

4. A process as claimed in claim 1 carried out in a heterogeneous system in which the compound of formula II is in solution in a water immiscible solvent and the hydroxide is in aqueous solution, the reaction being conducted in the presence of a quaternary ammonium salt which functions as a phase transfer catalyst.

5. A process as claimed in claim 1 which comprises the preliminary step of treating a compound of formula:

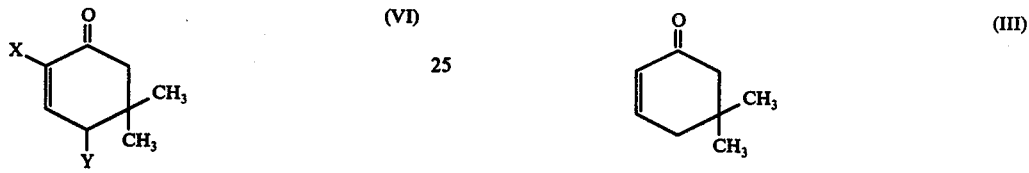

with a halogen of formula $Z_2$ wherein Z is chlorine or bromine to obtain a compound of formula II.

6. A process as claimed in claim 5 which comprises the preliminary step of treating a compound of formula:

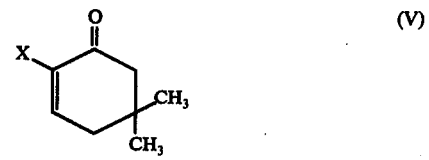

with N-chlorosuccinimide or N-bromosuccinimide to obtain a compound of formula VI.

7. A process as claimed in claim 6 which comprises the preliminary step of heating a compound of formula IV under reduced pressure to a sufficient temperature to cause elimination of hydrogen halide to obtain a compound of formula V.

8. A process as claimed in claim 7 which comprises the preliminary step of treating a compound of formula:

with a halogen of formula $X_2$ wherein X is chlorine or bromine to obtain a compound of formula IV.

* * * * *